(12) United States Patent
Heilman et al.

(10) Patent No.: US 9,957,361 B2
(45) Date of Patent: *May 1, 2018

(54) PROCESS FOR PRODUCING A WEB SUBSTRATE HAVING INDICIA DISPOSED THEREON AND ELASTIC-LIKE BEHAVIOR IMPARTED THERETO

(71) Applicant: The Procter & Gamble Company, Cincinnati, OH (US)

(72) Inventors: Laura Lynn Heilman, Petersburg, KY (US); Jill Marlene Orr, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/296,133

(22) Filed: Oct. 18, 2016

(65) Prior Publication Data

US 2017/0037209 A1    Feb. 9, 2017

Related U.S. Application Data

(60) Continuation of application No. 14/606,071, filed on Jan. 27, 2015, now Pat. No. 9,498,794, which is a
(Continued)

(51) Int. Cl.
*B29C 55/18* (2006.01)
*C08J 7/04* (2006.01)
(Continued)

(52) U.S. Cl.
CPC .......... *C08J 7/04* (2013.01); *A61F 13/51121* (2013.01); *A61F 13/51394* (2013.01);
(Continued)

(58) Field of Classification Search
CPC ...................................................... B29C 55/18
(Continued)

(56) References Cited

U.S. PATENT DOCUMENTS 2,585,915 A    2/1952  Chovannes
2,776,452 A    1/1957  Bredereck et al.
(Continued)

FOREIGN PATENT DOCUMENTS

EP           1586509      10/2005
WO       WO 95/13965      5/1995
(Continued)

OTHER PUBLICATIONS

PCT International Search Report, dated Mar. 4, 2009, 9 pages.
(Continued)

*Primary Examiner* — Jacob T Minskey
*Assistant Examiner* — Xue Liu
(74) *Attorney, Agent, or Firm* — Charles R. Ware

(57) ABSTRACT

A process for providing indicia and an elastic-like behavior to a web substrate is disclosed. The process comprises the steps of: providing a web substrate; printing indicia on the web substrate; and, providing the web substrate with a plurality of first regions and a plurality of second regions comprising the same material composition. A portion of the first regions extend in a first direction while the remainder of the first regions extend in a second direction perpendicular to the first direction to intersect one another. The first regions form a boundary completely surrounding the second regions. The second regions comprise a plurality of raised rib-like elements. The first regions undergo a molecular level and geometric deformation and the second regions initially undergo a substantially geometric deformation when the web material is subjected to an applied elongation along at least one axis.

12 Claims, 8 Drawing Sheets

Related U.S. Application Data division of application No. 13/079,221, filed on Apr. 4, 2011, now abandoned, which is a division of application No. 11/973,659, filed on Oct. 10, 2007, now Pat. No. 7,938,635, which is a continuation-in-part of application No. 10/737,430, filed on Dec. 16, 2003, now Pat. No. 7,410,683, which is a continuation-in-part of application No. 10/610,299, filed on Jun. 30, 2003, now abandoned, which is a continuation-in-part of application No. 10/324,661, filed on Dec. 20, 2002, now abandoned.

(51) Int. Cl.

| | | |
|---|---|---|
| *A61K 8/02* | (2006.01) | |
| *A61Q 5/00* | (2006.01) | |
| *A61Q 5/02* | (2006.01) | |
| *A61Q 19/00* | (2006.01) | |
| *A61Q 19/10* | (2006.01) | |
| *B31F 1/07* | (2006.01) | |
| *B41F 9/00* | (2006.01) | |
| *B41F 19/06* | (2006.01) | |
| *D04H 11/08* | (2006.01) | |
| *B05D 5/00* | (2006.01) | |
| *B05D 3/00* | (2006.01) | |
| *B65D 65/42* | (2006.01) | |
| *A47K 10/32* | (2006.01) | |
| *A61F 13/534* | (2006.01) | |
| *A61F 13/51* | (2006.01) | |
| *A61F 13/511* | (2006.01) | |
| *A61F 13/513* | (2006.01) | |

(52) U.S. Cl.
CPC .............. *A61K 8/0208* (2013.01); *A61Q 5/00* (2013.01); *A61Q 5/02* (2013.01); *A61Q 19/00* (2013.01); *A61Q 19/10* (2013.01); *B05D 3/002* (2013.01); *B05D 5/00* (2013.01); *B29C 55/18* (2013.01); *B31F 1/07* (2013.01); *B41F 9/003* (2013.01); *B41F 19/062* (2013.01); *B65D 65/42* (2013.01); *D04H 11/08* (2013.01); *A47K 2010/3266* (2013.01); *A61F 13/53436* (2013.01); *A61F 2013/51007* (2013.01); *A61F 2013/51178* (2013.01); *A61F 2013/51344* (2013.01); *A61F 2013/51366* (2013.01); *B31F 2201/0733* (2013.01); *B31F 2201/0743* (2013.01); *B31F 2201/0792* (2013.01); *C08J 2300/00* (2013.01); *Y10T 428/2457* (2015.01); *Y10T 428/24355* (2015.01); *Y10T 428/24405* (2015.01); *Y10T 428/24628* (2015.01); *Y10T 428/24802* (2015.01)

(58) Field of Classification Search
USPC ........................................................ 264/132
See application file for complete search history.

(56) References Cited

U.S. PATENT DOCUMENTS

| | | |
|---|---|---|
| 2,809,392 A | 10/1957 | Armstrong |
| 3,054,148 A | 9/1962 | Zimmerle et al. |
| 3,060,515 A | 10/1962 | Corbett |
| 3,281,257 A | 10/1966 | Rosen |
| 3,484,835 A | 12/1969 | Trounstine et al. |
| 3,773,608 A | 11/1973 | Yoshimura et al. |
| 3,857,144 A | 12/1974 | Bustin |
| 4,151,240 A | 4/1979 | Lucas et al. |
| 4,168,000 A | 9/1979 | MacRitchie |
| 4,214,945 A | 7/1980 | Lucas et al. |
| 4,233,017 A | 11/1980 | Lucas et al. |
| 4,326,664 A | 4/1982 | Benoit et al. |
| 4,376,147 A | 3/1983 | Byrne et al. |
| 4,401,427 A | 8/1983 | Benoit et al. |
| 4,463,045 A | 7/1984 | Ahr et al. |
| 4,546,029 A | 10/1985 | Cancio et al. |
| 4,609,518 A | 9/1986 | Curro et al. |
| 5,003,915 A | 4/1991 | D'Amato |
| 5,024,799 A | 6/1991 | Harp et al. |
| 5,108,814 A | 4/1992 | Harp et al. |
| 5,143,774 A | 9/1992 | Cancio et al. |
| 5,202,173 A | 4/1993 | Wu et al. |
| 5,205,650 A | 4/1993 | Rasmussen |
| 5,296,184 A | 3/1994 | Wu et al. |
| 5,330,133 A | 7/1994 | Rasmussen |
| 5,508,080 A | 4/1996 | Sorimachi et al. |
| 5,518,801 A | 5/1996 | Chappell et al. |
| 5,531,393 A | 7/1996 | Salzsauler et al. |
| 5,554,093 A | 9/1996 | Porchia et al. |
| 5,618,111 A | 4/1997 | Porchia et al. |
| 5,650,214 A | 7/1997 | Anderson et al. |
| 5,693,405 A | 12/1997 | Harvie et al. |
| 5,723,087 A | 3/1998 | Chappell et al. |
| 5,891,544 A | 4/1999 | Chappell et al. |
| 5,916,663 A | 6/1999 | Chappell et al. |
| 5,968,607 A | 10/1999 | Lovison |
| 6,027,483 A | 2/2000 | Chappell et al. |
| 6,234,676 B1 | 5/2001 | Galomb et al. |
| 6,314,879 B1 | 11/2001 | Siler et al. |
| 6,387,463 B1 | 5/2002 | Weder |
| 6,394,652 B2 | 5/2002 | Meyer et al. |
| 6,403,207 B1 | 6/2002 | Weder |
| 6,406,651 B1 | 6/2002 | Weder |
| 6,425,967 B1 | 7/2002 | Weder |
| 6,458,447 B1 | 10/2002 | Cabell et al. |
| 6,495,248 B1 | 12/2002 | Weder |
| 6,511,235 B2 | 1/2003 | Wu et al. |
| 6,520,330 B1 | 2/2003 | Batra |
| 6,521,307 B2 | 2/2003 | Weder |
| 6,531,025 B1 | 3/2003 | Lender et al. |
| 6,565,958 B1 | 5/2003 | Weder |
| 6,565,963 B2 | 5/2003 | Weder |
| 6,579,603 B1 | 6/2003 | Weder |
| 6,598,372 B2 | 7/2003 | Weder |
| 6,613,409 B2 | 9/2003 | Weder |
| 6,649,242 B2 | 11/2003 | Weder |
| 6,691,035 B1 | 2/2004 | Kang |
| 6,702,919 B2 | 3/2004 | Weder |
| 6,706,379 B2 | 3/2004 | Weder |
| 6,708,464 B2 | 3/2004 | Weder |
| 6,715,261 B2 | 4/2004 | Weder |
| 6,716,203 B2 | 4/2004 | Sorebo et al. |
| 6,720,051 B2 | 4/2004 | Weder |
| 6,723,417 B2 | 4/2004 | Weder |
| 6,753,074 B1 | 6/2004 | Weder |
| 6,755,006 B2 | 6/2004 | Weder |
| 6,755,350 B2 | 6/2004 | Rochford et al. |
| 6,902,644 B2 | 6/2005 | Weder |
| 6,983,686 B2 | 1/2006 | Vaughn et al. |
| 7,014,910 B2 | 3/2006 | Rochford et al. |
| 7,100,507 B1 | 9/2006 | Rochon et al. |
| 7,172,073 B2 | 2/2007 | Hanson |
| 7,410,683 B2 | 8/2008 | Curro et al. |
| 7,633,648 B2 | 12/2009 | Sasanuma et al. |
| 7,938,635 B2 | 5/2011 | Heilman et al. |
| 9,498,794 B2 | 11/2016 | Heilman et al. |
| 2002/0025752 A1 | 2/2002 | Taniguchi |
| 2002/0028230 A1 | 3/2002 | Eichhorn et al. |
| 2003/0067157 A1 | 4/2003 | McKillip |
| 2003/0072918 A1 | 4/2003 | Andersson |
| 2003/0120241 A1 | 6/2003 | Sorebo et al. |
| 2003/0122371 A1 | 7/2003 | Rochford et al. |
| 2004/0099388 A1 | 5/2004 | Chen |
| 2004/0261639 A1 | 12/2004 | Vaughn et al. |
| 2005/0121347 A1 | 6/2005 | Hanson |
| 2005/0145523 A1 | 7/2005 | Zander et al. |
| 2005/0154365 A1 | 7/2005 | Zander et al. |
| 2005/0178493 A1 | 8/2005 | Broering et al. |
| 2006/0093766 A1 | 5/2006 | Savicki et al. |

(56) References Cited

U.S. PATENT DOCUMENTS

| | | |
|---|---|---|
| 2006/0144736 A1 | 7/2006 | Goodrich et al. |
| 2006/0286343 A1 | 12/2006 | Curro et al. |
| 2007/0012715 A1 | 1/2007 | Dubreuil et al. |
| 2011/0206904 A1 | 8/2011 | Heilman et al. |

FOREIGN PATENT DOCUMENTS

| | | |
|---|---|---|
| WO | WO 03/031203 | 4/2003 |
| WO | WO 2004/045981 A1 | 6/2004 |
| WO | WO 2005/080071 | 9/2005 |
| WO | WO 2007/137624 A | 12/2007 |

OTHER PUBLICATIONS

Pantone Inc. Press Release: Color Just Got Bigger for 2005 with the New PANTONE Color Guides, Jan. 24, 2005, Carlstadt, N.J. USA—online at http://pk.pantone.com/pages/pantone/pantone.aspx?pg=20265&ca=10.

All Office Actions and Notice of Allowance in U.S. Appl. No. 14/606,071, filed Jan. 27, 2015.

PROCESS FOR PRODUCING A WEB SUBSTRATE HAVING INDICIA DISPOSED THEREON AND ELASTIC-LIKE BEHAVIOR IMPARTED THERETO

FIELD OF THE INVENTION

This invention relates to web substrates and more particularly to such web substrates having an indicia printed thereon and wherein the inherent elongation properties of the web substrate may be modified. More particularly, the present invention relates to apparati and processes suitable for the manufacture of web substrates suitable for the packaging of consumer products in which the web substrate is provided with indicia thereon and is subsequently treated by mechanical deformation in which the resistive force exerted by the web material to an applied elongation force can be modified. The indicia printed upon the web substrate may be positioned in registration with portions of the web substrate in which the inherent elongation properties of the web substrate have been modified.

BACKGROUND OF THE INVENTION

The term "flexible" is utilized herein to refer to materials that are capable of being flexed or bent especially repeatedly such that they are pliant and usable in response to externally applied forces. Accordingly, "flexible" is substantially opposite in meaning to terms such as "inflexible", "rigid", or "unyielding". Materials and structures that are flexible therefore may be altered in shape and structure to accommodate external forces and to conform to the shape of objects brought into contact with them without losing their integrity. Flexible films of the type commonly available are typically formed from materials having consistent physical properties throughout the film structure, such as stretch, tensile and/or elongation properties.

A process known for forming flexible film web substrates having deformations formed thereon include the passing of a continuous web material between a pair of matched forming rolls to form an intentional pattern of deformations in the film. Illustrative publications dealing with the state of the art with regard to continuous webs and film materials having intentional patterns and deformations disposed thereon are detailed in U.S. Pat. Nos. 5,554,093; 5,575,747; 5,723,087; 5,518, 801; 5,156,793; 7,172,801 and 6,394,652.

Likewise, printed film materials can be produced by several processes. A first process for printing a web substrate is the use of a rotogravure process. A rotogravure process is a true "intaglio" (i.e., cut-in or sunken) printing process. Rotogravure processes print directly from unconnected cells engraved into a plate cylinder. Ink is then applied to the engraved areas and doctored, or wiped off, the smooth non-image areas. The resulting inked image is then impressed onto the substrate to be printed. Typical print cylinders in rotogravure processes are machined, electroplated with copper, ground, and polished. The cells holding the ink are not interconnected; therefore, a checkerboard or saw tooth pattern shows up around the print edges—a characteristic of gravure printing. To overcome these deficiencies, very fine screen sizes are used to make the rough edges as inconspicuous as possible. The cylinder's print areas are etched as microscopic cup-like cells while non-print areas remain untouched: the larger and bolder the copy, the larger and deeper the etched cells. Fine tonal areas typically have a smaller cell size and depth. As would be known to those of skill in the art, inks suitable for use in a rotogravure process are fluid and have very low viscosity.

A second process for printing web substrates involves flexographic methods. Flexographic printing methods are methods of direct rotary printing that use resilient relief-image plates of rubber or photopolymer materials. The plates are affixed to plate cylinders and are inked by a cell-structured ink metering "anilox" roll carrying a fast drying fluid ink to plates that print onto virtually any substrate, absorbent or non-absorbent. An image is produced for every revolution of the printing plate cylinder. The printing plate cylinder is typically suitable for re-use with multiple designs depending upon the repeat pattern and web material width. Flexographic processes were developed primarily for printing onto packaging substrates where materials are commonly supplied in roll form for feeding into form/fill, overwrapping, bag making, and other continuous web processing machinery. As would be known to those of skill in the art, flexographic printing processes use either solvent or water-based low viscosity inks that dry very quickly between the print stations of a press.

Typical texturing processes for providing a printed web substrate with and elastic-like behavior can cause deformations in the printed surface, thereby obscuring any indicia disposed upon the web substrate. Particularly, the loss of branding indicia, consumer information indicia, patent marking statement indicia, and the like upon such packaging by an texturing process is an undesirable effect.

Accordingly, it is desirable to provide for a textured and printed substrate wherein the benefits of an "elastic-like" behavior in the direction of an applied elongation to the web substrate can be presented into such a material that does not obscure any indicia presented thereon. As used herein, the term "elastic-like" describes the behavior of web materials which, when subjected to an applied elongation, extend in the direction of applied elongation and when the applied elongation is released, the web materials return to a substantial degree to their untensioned condition. While such web materials exhibiting an elastic-like behavior would have a wide range of utility (such as covering materials such as upholstery, wrapping materials for complex shapes, commercial packaging, and the like), they would be particularly well suited for providing indicia-laden consumer packaging with an ability to be gripped as well as reduce the amount of breakthrough when the packaging is handled by the consumer.

SUMMARY OF THE INVENTION

The present disclosure provides a process for providing indicia and an elastic-like behavior to a web substrate. The process comprises the steps of: providing a web substrate; printing indicia on the web substrate; and, providing the web substrate with a plurality of first regions and a plurality of second regions comprising the same material composition. A portion of the first regions extend in a first direction while the remainder of the first regions extend in a second direction perpendicular to the first direction to intersect one another. The first regions form a boundary completely surrounding the second regions. The second regions comprise a plurality of raised rib-like elements. The first regions undergo a molecular level and geometric deformation and the second regions initially undergo a substantially geometric deformation when the web material is subjected to an applied elongation along at least one axis.

The present disclosure also provides a web substrate for containing a plurality of consumer goods. The web substrate comprises indicia printed on a surface of the web substrate and a plurality of first regions and a plurality of second regions disposed upon at least a portion of the web substrate. The plurality of first regions and plurality of second regions comprise the same material composition. A portion of the first regions extend in a first direction while the remainder of the first regions extend in a second direction perpendicular to the first direction to intersect one another. The first regions form a boundary completely surrounding the second regions. The second regions comprise a plurality of raised rib-like elements. The first regions undergo a molecular level and geometric deformation and the second regions initially undergo a substantially geometric deformation when the web material is subjected to an applied elongation along at least one axis. The indicia provides a branding signal to a consumer;

DETAILED DESCRIPTION OF THE INVENTION

Figure 1:
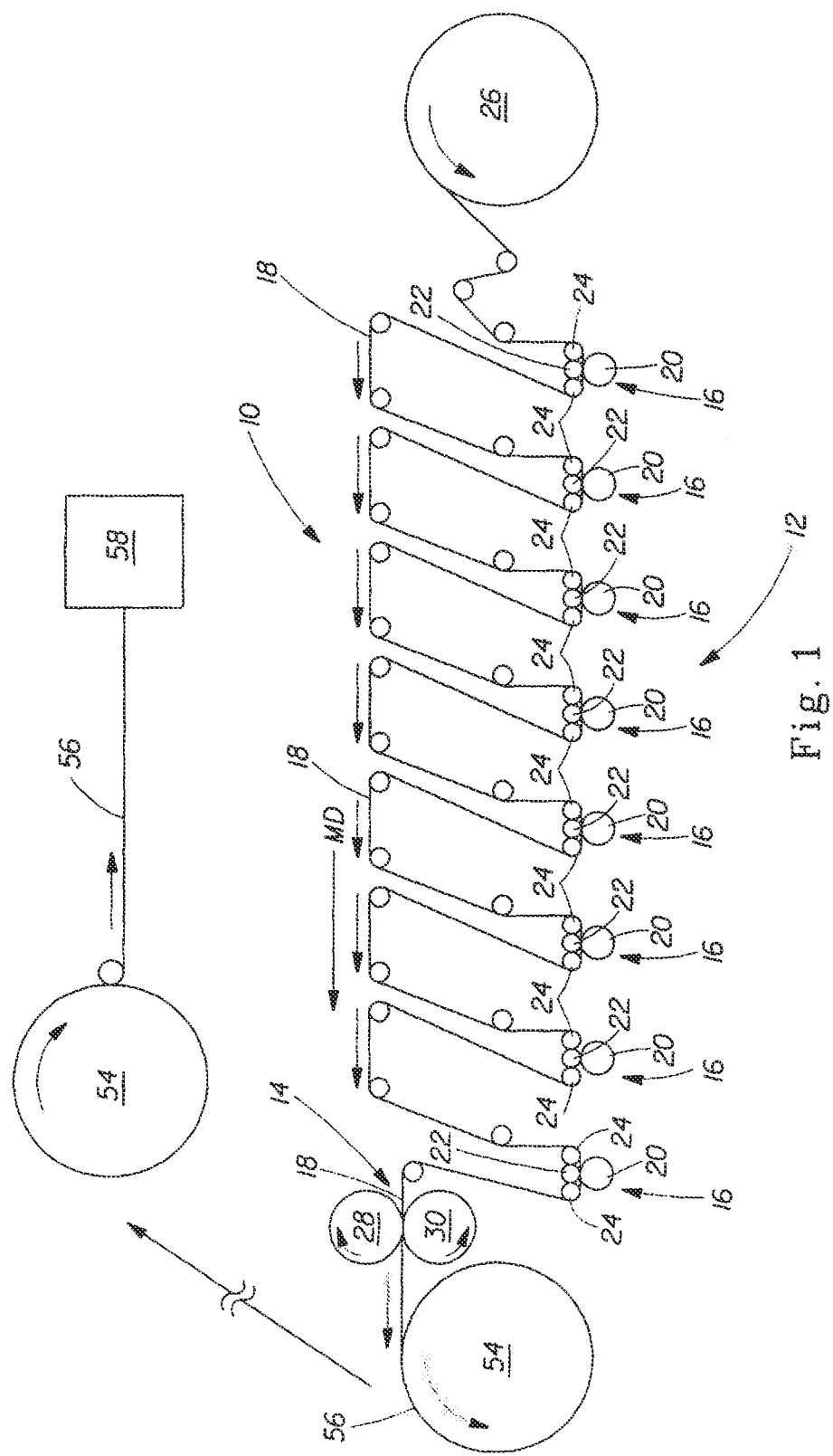
FIG. 1 is a sectional view of an exemplary printing and apparatus for imparting elastic-like behavior of the present invention.

FIG. 1 illustrates an embodiment of an apparatus for printing and imparting elastic-like behavior 10 in accordance with the present invention. As shown, the apparatus for printing and imparting elastic-like behavior 10 can be provided with an exemplary rotogravure printing apparatus 12 and an exemplary apparatus for imparting elastic-like behavior 10. The exemplary rotogravure printing apparatus 12 can be provided with at least one print station 16. However, one of skill in the art will understand that preferably, a rotogravure printing apparatus 12 may be provided with a plurality of print stations 16, as may be required by the needs of the printing process, the operator, and/or the final product. For example, an exemplary rotogravure printing apparatus 12 may comprise as few as one print station 16 or may comprise as many as eight print stations 16. For purposes of the instant invention, it is irrelevant as to the number of print stations 16 utilized with rotogravure printing apparatus 12, but rather it is relevant that the number of print stations 16 be sufficient in order to provide for the appropriate indicia to be applied to a web substrate 18 that is printed by the rotogravure printing apparatus 12 of the instant invention.

An exemplary (or in the alternative, each) print station 16 is preferably provided with a cylindrical printing roller 20. By way of example, an ink may be provided to a cylindrical ink roller (not shown) by an ink applicator (not shown) that applies ink to the ink roller. The ink applicator may be, for example, a chambered doctor blade or other conventional ink applying device. Typically, an ink roller is rotatably supported by a support frame so that the ink roller is in contact with the cylindrical printing roller 20. The support frame rotatably supports the cylindrical printing roller 20 adjacent to a cylindrical backing roller (not shown). A web substrate 18 to which the ink is to be applied passes through the nip formed between the cylindrical printing roller 20 and a backing roller 22. The web substrate 18 may be supported or directed by a plurality of support rollers 24. As would be known to one of skill in the art, the rotogravure apparatus 12 may also include a conventional dryer (not shown) for drying the ink after it is applied to the web substrate 18. A dryer may be provided at the exit of each succeeding print station 16 or over a plurality of print stations 16 as required by the operation or the operator. Similarly, a conventional cooling apparatus (not shown), such as that disclosed in U.S. Pat. No. 5,881,647, for cooling the web substrate 18 after it passes through the dryer can be provided as required After unwinding a web substrate 18 from a wound parent roll 26, the web substrate 18 is provided in contacting engagement with each successive print station 16 comprising the rotogravure printing apparatus 12 as may be required to provide for the required indicia to be disposed upon web substrate 18. After the required indicia are disposed upon web substrate 18, the web substrate 18 is presented to the apparatus for imparting elastic-like behavior 14. An exemplary apparatus for imparting elastic-like behavior 14 is provided with a pair of intermeshing rollers 28, 30. Intermeshing rollers 28, 30 are provided with a plurality of intermeshing teeth (not shown). Intermeshing rollers 28, 30 are brought together under pressure to form the web substrate 18 of the present invention.

Figure 5:
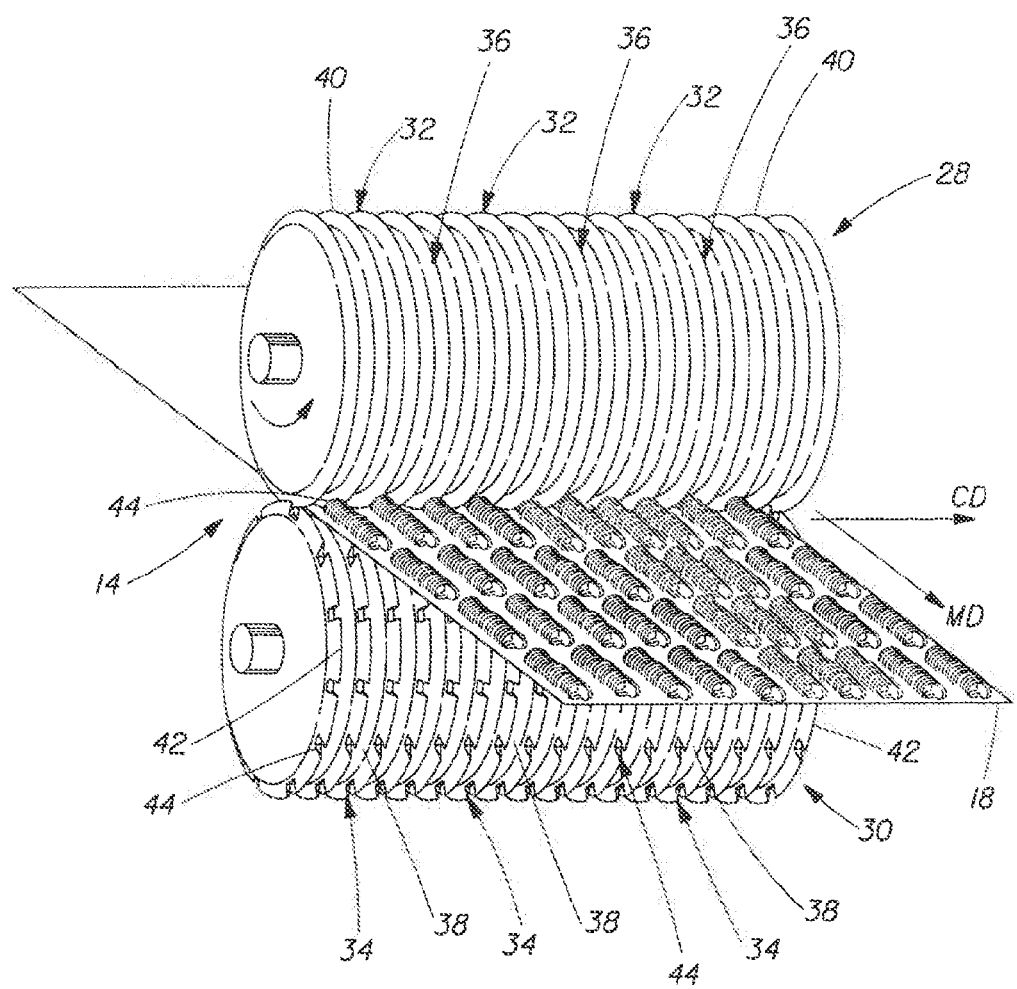
FIG. 5 is a perspective view of a preferred apparatus used to provide web materials of the present invention with elastic-like behavior.
Figure 6:
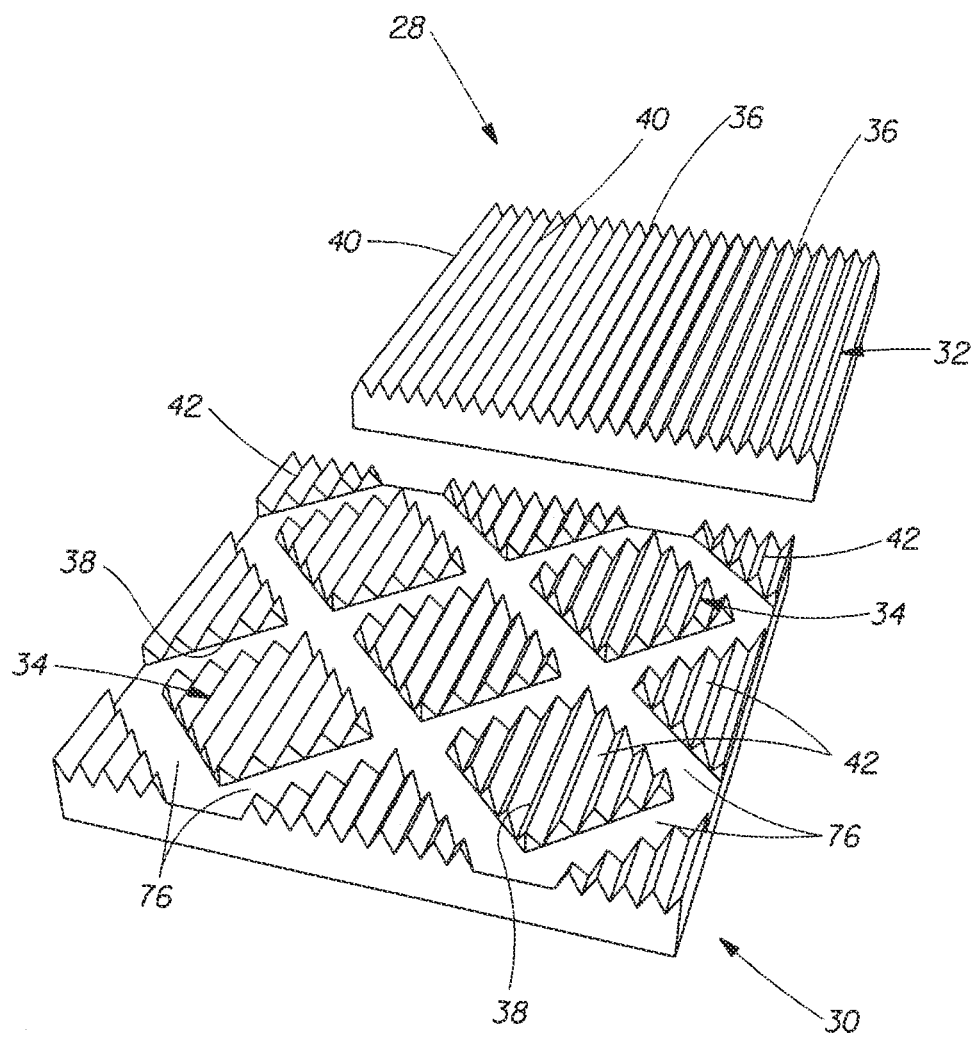
FIG. 6 is a perspective view of an exemplary surface suitable for a preferred apparatus for providing elastic-like behavior to a web substrate.

Turning to FIG. 5, the apparatus for imparting elastic-like behavior 14 is provided with intermeshing rollers 28, 30. In an exemplary embodiment, intermeshing roller 28 includes tooth regions 32 and grooved regions 36. The tooth regions 32 are preferably provided with a plurality of teeth 40 that mesh with teeth 42 of intermeshing roller 30. As shown in FIG. 6, the surfaces of intermeshing roller 28 and intermeshing roller 30 can be provided with one, or a plurality, of discreet toothed regions 32, 34, respectively, and grooved regions 36, 38, respectively, such that toothed region 32 of intermeshing roller 28 is provided with teeth 40 that mesh with teeth 42 of intermeshing roll 30. Thus, when a web substrate 18 is positioned between intermeshing roller 28 and intermeshing roller 30, the portions of the web substrate 18 that are positioned within grooved regions 36 and/or toothed regions 32 of intermeshing roller 28 and void region 76 of intermeshing roller 30 remain undeformed. These regions correspond with the first regions 44 of web substrate 18, shown in FIG. 8. The portions of the web substrate 18 positioned between teeth 40 of toothed region 32 of intermeshing roller 28 and teeth 42 of intermeshing roller 30 are incrementally and plastically deformed creating rib-like elements 46 in the second regions 48 of the web substrate 18. One of skill in the art would appreciate that some materials are less able to withstand the high rate of strain experienced in the process for imparting elastic-like behavior to the web substrate. In such cases, it should be realized that alternatives to one or both of intermeshing rollers 28, 30 can be incorporated into the apparatus for imparting elastic-like behavior 14, such as, for example, belts, conveyors, or multiple rolls.

Turning to FIG. 6, an exemplary apparatus for printing and imparting elastic-like behavior 10 useful for the present invention provides for a pair of intermeshing rollers 28, 30. For exemplary purposes only, intermeshing rollers 28, 30 can be provided with surfaces such as those shown. In this example, intermeshing roller 28 may be provided with a plurality of toothed regions 32 and a plurality of grooved regions 36 that extend substantially parallel to a longitudinal axis running through the center of the cylindrical intermeshing roller 28. Toothed region 32 preferably includes a plurality of teeth 40. Further, intermeshing roller 30 may be provided with a plurality of teeth 42 that mesh with teeth 40 on intermeshing roller 28. As a web substrate is passed between intermeshing roller 28 and intermeshing roller 30, the void region 76 disposed upon the surface of intermeshing roller 30 will leave portions of the web substrate 18 unformed producing the first regions 44 of the web substrate 18 of the present invention. The portions of the web substrate 18 passing between toothed region 32 and toothed region 34 will be formed by teeth 40 and 42, respectively, producing rib-like elements 46 in the second regions 48 of the web substrate 18.

In a preferred embodiment of the present invention, the apparatus for imparting elastic-like behavior 14 preferably provides web substrate 18 with an elastic-like behavior so that the web substrate 18 of the present invention may exhibit an initial elongation and partial recovery which results in the web substrate 18 not returning to its untensioned length; that is, the web substrate 18 has undergone a degree of permanent set or deformation and has a new longer untensioned length. The web substrate 18 may exhibit an elastic-like behavior in response to subsequent elongations of the web substrate 18 beyond the new longer untensioned length.

Another elastic-like behavior that can be exhibited by web substrate 18 is an elongation and recovery with a definite and sudden increase in the force resisting elongation where this definite and sudden increase in resistive force restricts further elongation against relatively small elongation forces. The definite and sudden increase in the force resisting elongation is referred to as a "force wall". As used herein, the term "force wall" refers to the behavior of the resistive force of a web material during elongation wherein at some point in the elongation distinct from the untensioned or starting point the force resisting the applied elongation suddenly increases. After reaching the force wall, additional elongation of the web substrate 18 is only accomplished via an increase in the elongation force to overcome the higher resistive force of the web substrate 18.

Figure 7:
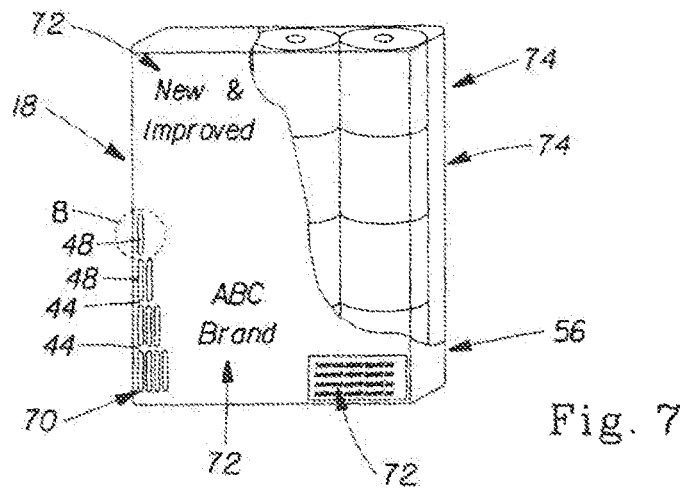
FIG. 7 is a plan view of an exemplary consumer products packaging embodying the web material having indicia and an elastic-like behavior imparted thereto.
Figure 8:
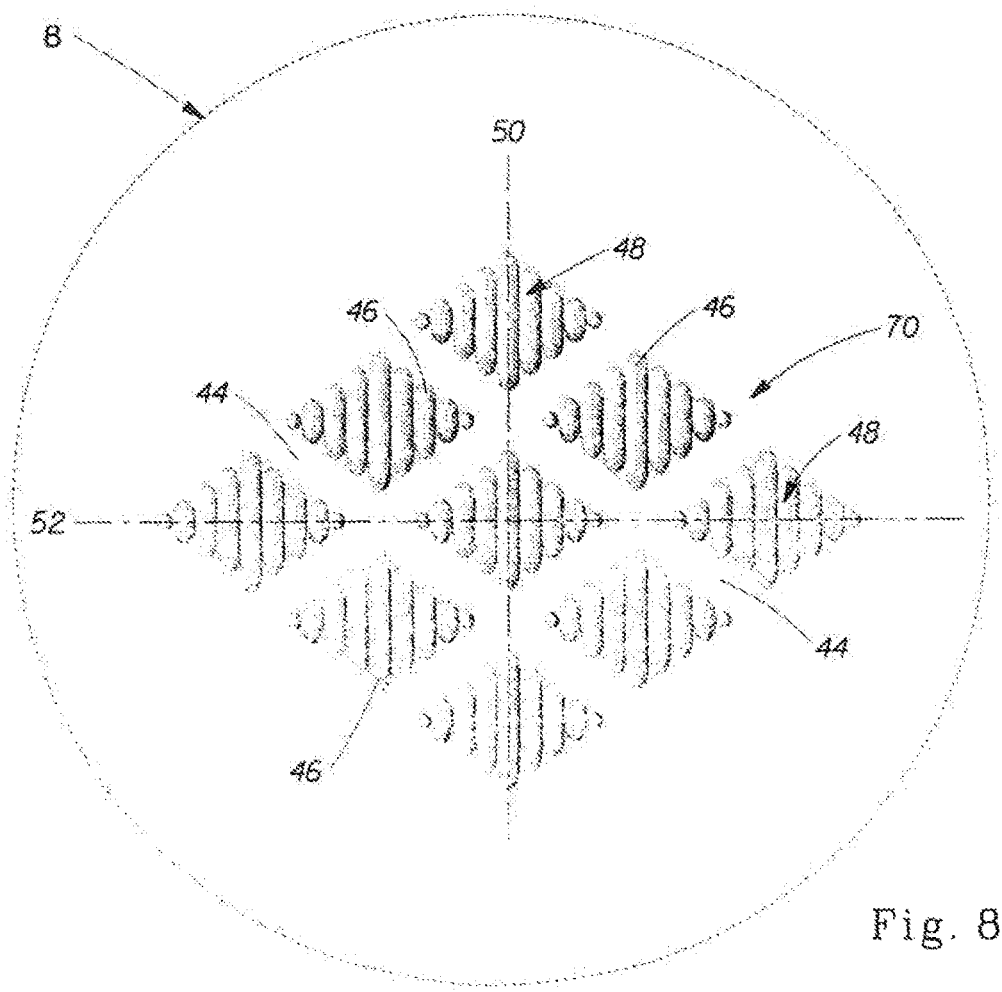
FIG. 8 is an expanded view of the region labeled 8 in FIG. 7.

As shown in FIGS. 7 and 8, the web substrate 18 of the present invention preferably includes a strainable network 70 having at least two distinct and dissimilar regions comprised of the same material composition. The first region 44 is preferably oriented substantially parallel to an axis of elongation such that it will undergo a molecular level deformation in response to an applied axial elongation in a direction substantially parallel to the elongation axis before a substantial portion of the second regions 48 undergoes any substantial molecular level deformation. As used herein, the term "substantially parallel" refers to an orientation between the two axes whereby the subtended angle formed by the two axes or an extension of the two axes is less than 45°. In the case of a curvilinear element, it may be more convenient to use a linear axis which represents an average of the curvilinear element. The second regions 48 initially undergo a substantially geometric deformation in response to an applied elongation in the direction substantially parallel to the axis. However, it should be readily realized that first regions 44 may be aligned at any angular relationship to the axis of elongation. It is not intended that the orientation of first regions 44 be critical to the operation of the instant invention. Rather, it is important that first regions 44 be provided in such an orientation that first regions 44 undergo a molecular level deformation in response to an applied axial elongation before a substantial portion of the second regions 48 undergo any substantial molecular level deformation. Thus, the first regions 44 may be oriented substantially or non-substantially parallel any axis of elongation.

In the preferred embodiment of the present invention shown in FIG. 8, the second region 48 is comprised of a plurality of raised rib-like elements. As used herein, the term "rib-like element" refers to an embossment, debossment, or combination thereof, which has a major axis and a minor axis. Preferably, the major axis is at least as long as the minor axis. The major axis of the rib-like elements 46 are preferably oriented substantially perpendicular to the axis of applied elongation. The major axis and the minor axis of the rib-like elements 46 may each be linear, curvilinear, or a combination of linear and curvilinear. As used herein, the term "substantially perpendicular" refers to an orientation between two axes whereby the subtended angle formed by the two axes or an extension of the two axes is greater than 45°. In the case of a curvilinear element, it may be more convenient to use a linear axis which represents an average of the curvilinear element.

The rib-like elements allow the second regions 48 to undergo a substantially "geometric deformation" which results in significantly less resistive forces to an applied elongation than that exhibited by the "molecular level deformation" of the first region 44. As used herein, the "molecular level deformation" refers to deformation which occurs on a molecular level that is not discernible to the normal naked eye; that is, even though one may be able to discern the effect of molecular level deformation (e.g., elongation of the web material), one is not able to discern the deformation which allows or causes it to happen. This is in contrast to the term "geometric deformation". As used herein, the term "geometric deformation" refers to deformations of the web substrate 18 that are generally discernible to the normal naked eye when the web substrate 18 or articles embodying the web substrate 18 are subjected to an applied elongation. Types of geometric deformation include, but are not limited to, bending, unfolding, and rotating.

Yet another elastic-like behavior that the web substrate 18 of the present invention may exhibit is an elongation and recovery with two or more distinctive force walls. This type of elastic-like behavior would be experienced if, for example, after reaching a first force wall sufficient elongation force was applied to overcome the first force wall and continue to elongate the web substrate 18 until a second force wall was encountered.

When the web substrate 18 of the present invention has multiple or staged force walls, rib-like elements 46 in one or more of the second regions 48 reach their limit of geometric deformation and become essentially co-planar with the material in the first regions 44, thereby causing the web substrate 18 to exhibit a first force wall. Further elongation of the web substrate 18 molecularly deforms the rib-like elements 46 which have reached their limit of geometric deformation and simultaneously geometrically deforms the rib-like elements 46 in the remaining second regions 48 until they reach their limit of geometric deformation, thereby causing the web substrate 18 to exhibit a second force wall.

In yet another embodiment of the present invention, the web substrate 18 exhibits at least two significantly different stages of resistive force to an applied elongation along at least one axis when subjected to an applied elongation in a direction substantially parallel to that axis. The web substrate 18 includes a strainable network having at least two distinct regions. One of the regions is configured such that it will exhibit resistive force in response to an applied axial elongation in a direction substantially parallel to the axis before a substantial portion of the other region develops any significant resistive force to the applied elongation. At least one of the regions has a surface path length which is greater than that of the other region as measured substantially parallel to the axis while the web substrate 18 is in an untensioned condition. The region exhibiting the longer surface path length includes one or more rib-like elements 46 that extend beyond the plane of the other region. The web substrate 18 exhibits a first resistive force to the applied elongation until the elongation of the web substrate 18 is sufficient to cause a substantial portion of the region having the longer surface path length to enter the axis of applied elongation, whereupon the web substrate 18 exhibits a second resistive force to further elongation. The total resistive force to elongation is higher than the first resistive force to elongation provided by the first region 44.

Preferably, the first regions 44 have a first surface path length L1 as measured substantially parallel to the axis of elongation while the web substrate 18 is in an untensioned condition. The second regions 48 have a second surface path length L2 as measured substantially parallel to the axis of elongation while the web substrate 18 is in an untensioned condition. The first surface path length L1 is less than the second surface path length L2. The first region 44 preferably has an elastic modulus E1 and a cross-sectional area A1. The first region 44 produces by itself a resistive force P1 due to molecular level deformation in response to an applied axial elongation D. The second regions 48 preferably have an elastic modulus E2 and a cross-sectional area A2. The second regions 48 produce a resistive force P2 due to geometric deformation in response to the applied axial elongation D. The resistive force P1 is significantly greater than the resistive force P2 so long as (L1+D) is less than L2.

Preferably, when (L1+D) is less than L2, the first region 44 provides for an initial force P1 in response to the applied axial elongation D substantially satisfying the equation P1=(A1×E1×D)/L1. When (L1+D) is greater than L2, the first and second regions 44, 48 provide a combined total resistive force PT to the applied axial elongation D satisfying the equation:

$$PT = \frac{(A1 \times E1 \times D)}{L1} + \frac{(A2 \times E2 \times |L1 + D - L2|)}{L2}$$

Preferably, the surface path length of the second region 48 is at least 15% greater than that of the first region 44 as measured parallel to the axis of elongation while the web substrate 18 is in an untensioned condition. More preferably, the surface path length of the second region 48 is at least about 30% greater than that of the first region 44 as measured parallel to the axis of elongation while the web substrate 18 is an untensioned condition.

Preferably, the first regions 44 are substantially planar; that is, the material within the first region 44 is in substantially the same condition before and after the formation step undergone by web substrate 18. The second regions 48 include a plurality of raised rib-like elements 46 that may be embossed, debossed, or provided as a combination thereof. The rib-like elements 46 have a first or major axis 50 which is substantially parallel to the transverse axis of the web substrate 18 and a second or minor axis 52 which is substantially parallel to the longitudinal axis of the web substrate 18. The major axis 50 of the rib-like elements 46 is at least equal and preferably longer than the minor axis 52. Preferably, the ratio of lengths of the major axis 50 and minor axis 52 is at least about 1:1 or greater and, more preferably, at least about 2:1 or greater.

The rib-like elements 46 disposed within second region 48 may be separated from one another by unformed areas (essentially unembossed or debossed) or simply formed as spacing areas. Preferably, the rib-like elements 46 are adjacent one another and are separated by an unformed area of less than 0.01" as measured perpendicular to the major axis 50 of the rib-like elements 46 and, more preferably, the rib-like elements 46 are contiguous having no unformed areas between them.

Further, the depth and frequency of the rib-like elements 46 can also be varied to control the available stretch of the web substrate 18 of the present invention. The available stretch is increased if for a given frequency of rib-like elements 46, the height or degree of formation imparted on the rib-like elements 46 is increased. Similarly, the available stretch is increased if for a given height or degree of formation, the frequency of the rib-like elements 46 is increased.

It should be realized that the particular web substrate 18 shown is an example of an elastic-like web of the present invention. The present invention is clearly not limited to the geometric deformations shown in the web substrate 18. Indeed, several alternative embodiments of web substrates 18 of the present invention can have any shape, design, or outcome of rib-like elements 46 as required to suit the intended purpose of the web substrate 18. Alternatively, the geometric deformation could consist of a more tuft-like structure.

In any regard, there are several functional properties that can be controlled to the application of the present invention. The functional properties of the web substrate 18 are the resistive force exerted by the web substrate 18 against an applied elongation and the available stretch of the web substrate 18 before a force wall is encountered. The resistive force that is exerted by the web substrate 18 against an applied elongation is a function of the material (e.g., composition, molecular structure, orientation, and the like), cross-sectional area, and the percent of the projected surface area of the web substrate 18 that is occupied by the first region 44. The higher the percent area coverage of the web substrate 18 by the first region 44, the higher the resistive force that the web substrate 18 will exert against an applied elongation for a given material, composition, and cross-sectional area. The percent coverage of the web substrate 18 by the first region 44 is determined in part, if not wholly, by the widths of the first region 44 and the spacing between adjacent first regions 44.

Further, the available stretch of the web substrate 18 is determined by the surface path length of the second region 48. The surface path length of the second region 48 is determined, at least in part, by the rib-like element 46 spacing, rib-like element 46 frequency, and depth of formation of the rib-like elements 46 as measured perpendicular to the plane of the web substrate 18. In general, the greater the surface path length of the second region 48, the greater the available stretch of the web substrate 18.

In certain embodiments, it may be desirable to provide a web substrate 18 having first regions 44, second regions 48, and/or rib-like elements 46 that are registered relative to areas of the web substrate having indicia 72 printed thereon. One of skill in the art would understand that it may be desirable in certain consumer products 74 to provide for first regions 44, second regions 48, and/or rib-like elements 46 upon web substrate 18 that are disposed in regions of lower print quality upon web substrate 18. In certain consumer products 74, one of skill in the art should understand that it may also be desirable to provide for first regions 44, second regions 48, and/or rib-like elements 46 upon web substrate 18 in regions of web substrate 18 having no indicia 72 printed thereon. However, one of skill in the art will understand that the degree of elastic-like behavior of the web substrate 18 of the instant invention can be adjusted as required to provide for the amount of elastic-like behavior necessary in order to accommodate the needs of the consumer product 74 contained within the printed and textured web substrate 56 bound thereabout and still provide for the increased ability of the consumer product 74 to be easily gripped and reduce the amount of breakthrough when the consumer product 74 is handled. This includes providing first regions 44, second regions 48, and/or rib-like elements 46 in regions of web substrate 18 having a high degree, or numbers, of indicia 72 printed thereon and yet not obscure the indicia 72.

Figure 9:
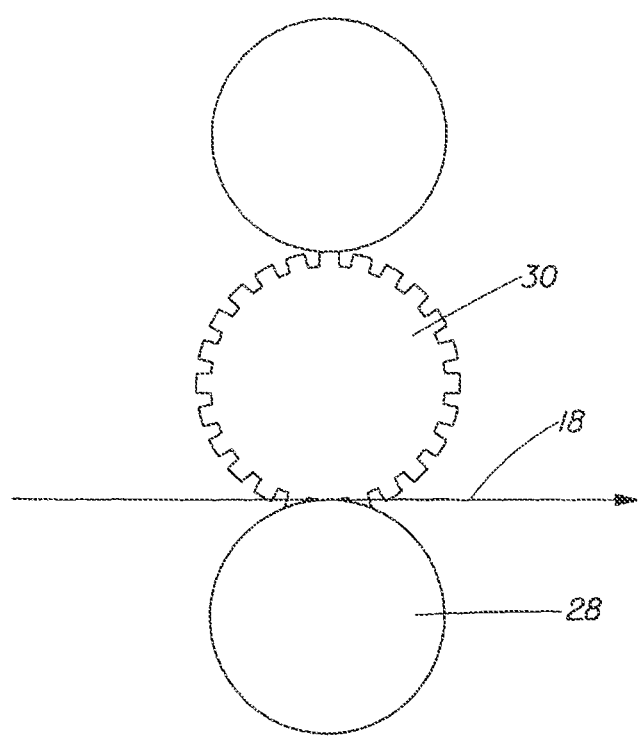
FIG. 9 is a sectional view of an alternative web substrate printing and apparatus for imparting elastic-like behavior.

Further, one of skill in the art would understand that either, or both of, intermeshing rollers 28, 30 could be provided with a plurality of holes or conduits that are in fluid communication with an ink to be disposed upon web substrate 18. In this exemplary embodiment, it would be possible to simultaneously dispose indicia 72 upon web substrate 18 while web substrate 18 is being processed by the apparatus for imparting elastic-like behavior 14. Processing web substrate 18 in this manner could facilitate the deposition of ink upon the web substrate 18 in the interstitial regions disposed between individual rib-like elements 46 and may further increase the quality of indicia 72 disposed upon web substrate 18. Alternatively, as shown in FIG. 9, either, or both, of intermeshing rollers 28, 30 could be put in surface contact with an ink source, such as an ink roller, in which the ink is deposited onto the peaks of the ridges of the intermeshing rollers 28, 30. The ink is then disposed upon the web substrate 18 while passing through the apparatus for printing and imparting elastic-like behavior 10. It should be realized that these processes could also be used to print on non-wovens or other materials. In addition to printing ink, the processes disclosed herein could be adapted by one of skill in the art to print or deposit other materials, such as lotions or glue that enhance the material aesthetics or performance.

Returning again to FIG. 1, the web substrate 18 having indicia 72 and first regions 44, second regions 48, and/or rib-like elements 46 disposed thereon may then be wound upon a second parent roll 54. At the user's discretion, the second parent roll 54 containing the printed and elastic-like, structurally modified web substrates 56 may be stored until needed for a manufacturing process 58. When the printed and elastic-like, structurally modified web substrate 56 produced by the present invention is required by the manufacturing process 58, it may be unwound from second parent roll 54 and directed towards manufacturing process 58, as required.

Figure 2:
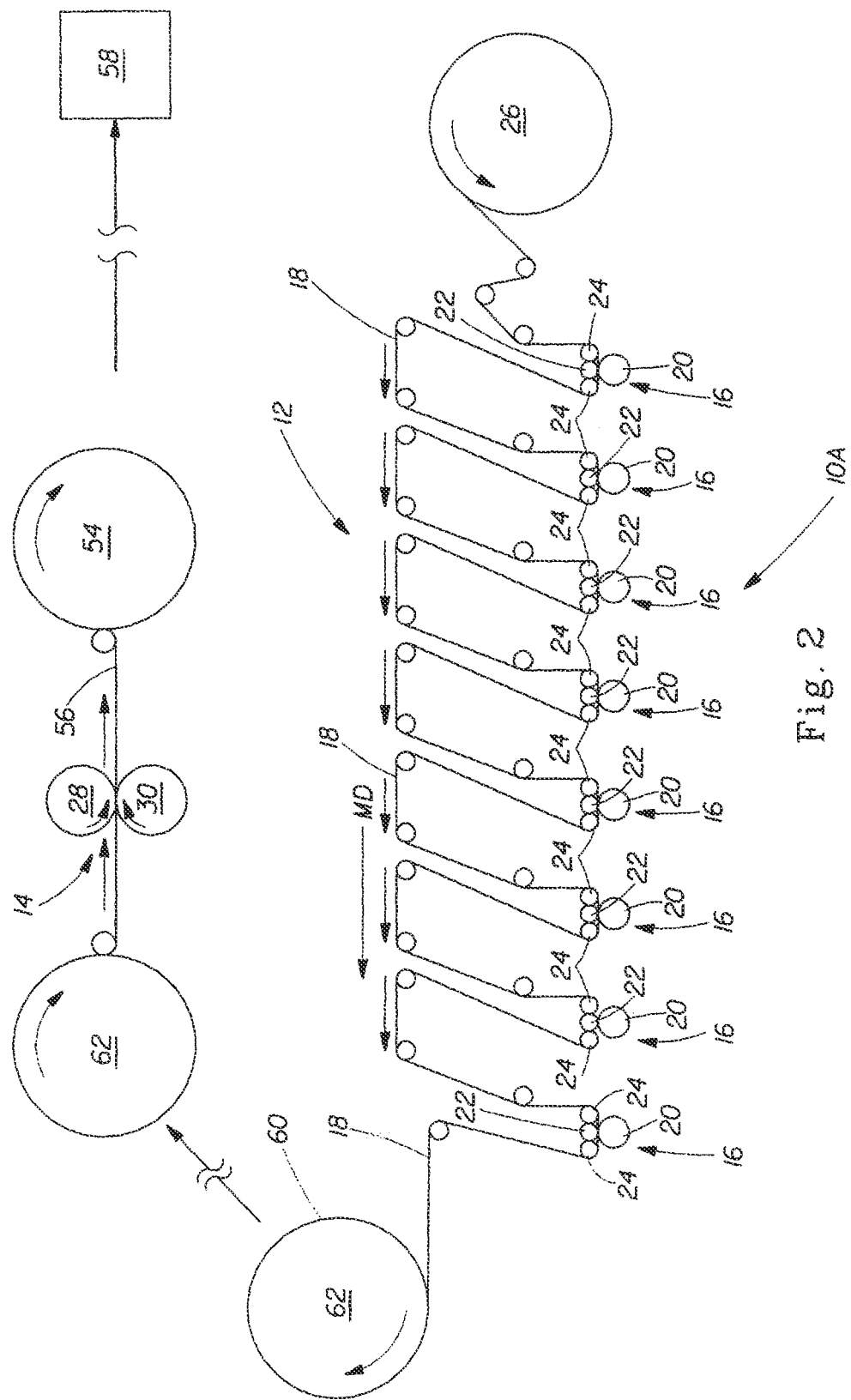
FIG. 2 is a sectional view of an alternative web printing and apparatus for imparting elastic-like behavior.

The apparatus for imparting elastic-like behavior 14 could be located prior to the rotogravure printing apparatus 12, between rotogravure printing apparatus 12 and a cooling apparatus (not shown), or between a cooling apparatus and second parent roll 54 and/or intermediate parent roll 62. In some cases, the heat imparted to the web material 18 during the printing and/or drying steps could improve the ability to impart the elastic-like behavior to the web substrate 18, and it could improve the aesthetics or performance of the textured portion of the web substrate 18. As shown in FIG. 2, an alternative apparatus for printing and imparting elastic-like behavior 10A of the instant invention can provide rotogravure printing apparatus 12 and the apparatus for imparting elastic-like behavior 14 as separate and isolated steps. In such an application, the web substrate 18 is unwound from a wound parent roll 26 and provided to a plurality of print stations 16. Each print station 16 provides for at least a portion of the desired indicia upon web substrate 18. Upon the completion of sufficient processing by print station (or stations) 16 as required, the printed web substrate 60 can then be wound upon intermediate parent roll 62. Then, as required, the intermediate parent roll 62, having printed web substrate 60 convolutely wound thereabout, can be separately processed by apparatus for printing and imparting elastic-like behavior 10 to provide for printed and textured web substrate 56 as described supra. Printed and elastic-like, structurally modified web substrate 56 can be then wound about second parent roll 54 and disposed as required to process 58. Alternatively, the printed web substrate 56 can be directed immediately to any manufacturing process 58 as required by the needs of the end user.

Figure 3:
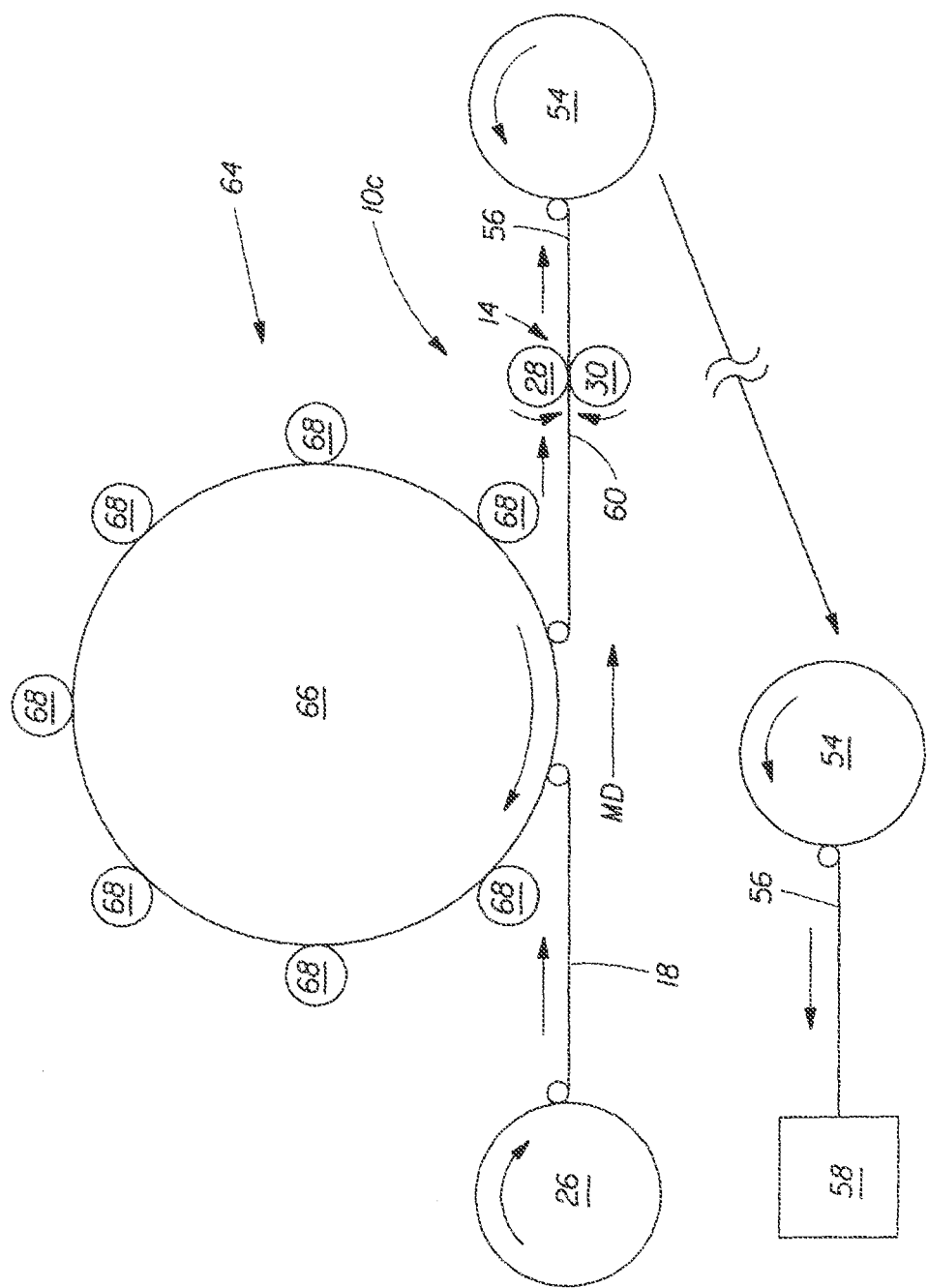
FIG. 3 is a sectional view of another alternative embodiment of an exemplary web substrate printing and apparatus for imparting elastic-like behavior.

FIG. 3 shows an exemplary apparatus for printing and imparting elastic-like behavior 10C. In the apparatus for printing and imparting elastic-like behavior 10C, a web substrate 18 is unwound from a wound parent roll 26 and presented to flexographic printing apparatus 64. The flexographic printing apparatus 64 comprises a central impression cylinder 66 surrounded by a plurality of printing units 68. Thus, the web substrate 18 is applied to the surface of central impression cylinder 66 and rotated about a longitudinal axis of central impression cylinder 66 so that web substrate 18 progresses from a first printing unit 68 toward succeeding printing units 68 disposed about the periphery of central impression cylinder 66. Each printing unit 68 can be coated with the appropriate ink necessary to provide indicia 72 that conveys the branding information or other desired information necessary upon a finally printed web substrate 60. In one embodiment, the ink is applied to a printing unit 68 by slot coating. Thus, by way of example, a first printing unit 68 disposed about central impression cylinder 66 can apply a first color to web substrate 18 and succeeding printing units 68 can apply additional colors as required to web substrate 18 as web substrate 18 passes between each individual printing unit 68 and central impression cylinder 66.

As known to those of skill in the art, each printing unit 68 may be provided with a plurality of printing plates that are disposed upon the exterior of each printing unit 68. Typically, a printing plate is provided with numerous small raised portions that transfer ink from an ink roller to the web substrate 18 in passing engagement thereto. Typically, the raised portions of the printing plate are non-uniform in shape and correspond to the desired image for indicia to be printed on the web substrate 18. The raised portions on the printing plate may be formed via a photosensitive etching process in which portions of the printing plate are selectively exposed to radiation with the unexposed portions being subsequently removed via an etching agent, thus leaving the raised portions behind. Typically, the total thickness of a printing plate is approximately ⅛" to 1/16". However, those of skill in the art will understand that the formation of raised portions of the printing plate suitable for use with each printing unit 68 may be formed with other processes as is known to those of skill in the art.

As shown in FIG. 7, indicia 72 may comprise information typically found upon consumer product packaging. By way of non-limiting example, indicia 72 may comprise a branding signal. Exemplary, but non-limiting branding signals, may include, brand information (i.e. brand names—trade names or trademarks including generic or descriptive language), product identification information, brand logos (i.e., brand names or brand logo that are normally associated with the primary product being sold or with a secondary product such as indicia associated with a particular product or product line. The brand logo may include any combination of words, symbols, pictures or other graphic or textual elements), patent marking statements, roll equivalency information, regulatory information, consumer product information (i.e., texture, absorbency, softness, caliper, biodegradability, hygiene, anti-microbial benefits, luxury, scent, moisturizing qualities, strength, and combinations thereof), packaging art work, as well as other visual representations or communicative indicia (i.e., including, but not limited to: brands, logos, brand logos, brand names, words, symbols, pictures, trademarks, graphics, text, product samples, advertising information, letters, messages, and combinations thereof), or other information that may indicate a value or may provide value to the overall packaging.

Returning again to FIG. 3, after all necessary inks are applied to web substrate 18 to form printed web substrate 60 to provide for indicia 72, the printed web substrate 60 can be provided with an elastic-like behavior by the apparatus for imparting elastic-like behavior 14, as described supra. The apparatus for printing and imparting elastic-like behavior 10 can provide printed web substrate 60 with a plurality of first regions 44 surrounding a plurality of second regions 48 having rib-like elements 46 disposed therein. The apparatus for imparting elastic-like behavior 14 could be located prior to the flexographic printing apparatus 64, between flexographic printing apparatus 64 and a cooling apparatus (not shown), or between a cooling apparatus and second parent roll 54 and/or intermediate parent roll 62. In some cases, the heat imparted to the web material 18 during the printing and/or drying steps could improve the ability to impart the elastic-like behavior to the web substrate 18, and it could improve the aesthetics or performance of the textured portion of the web substrate 18.

After providing the printed web substrate 60 with the required rib-like elements 46 either in registration or out of registration with any indicia 72 disposed upon web substrate 18 by the flexographic printing apparatus 64, the resulting printed and elastic-like, structurally modified web substrate 56 can then be wound into a second parent roll 54 for storage as required by the end user. Any registration requirements or needs of the rib-like elements 46 with any indicia 72 provided upon web substrate 18 can be provided to meet the needs of the consumer, consumer packaging, packaging operations or process as required. In some circumstances, it may be desirable to provide for rib-like elements 46 in regions of less indicia 72 upon web substrate 18. However, it should be clearly realized that rib-like elements 46 can be disposed upon any region of web substrate 18 having indicia 72 disposed thereon without affecting the overall quality and appearance of the final consumer product 74. Upon a defined need of the printed and elastic-like, structurally modified web substrate 56 disposed about second parent roll 54 (i.e., manufacturing process 58), the printed and elastic-like, structurally modified web substrate 56 can be then utilized by manufacturing process 58 as required. In a preferred embodiment, manufacturing process 58 utilizes the printed and elastic-like, structurally modified web substrate 56 as an overwrap for a plurality of consumer products 74.

Figure 4:
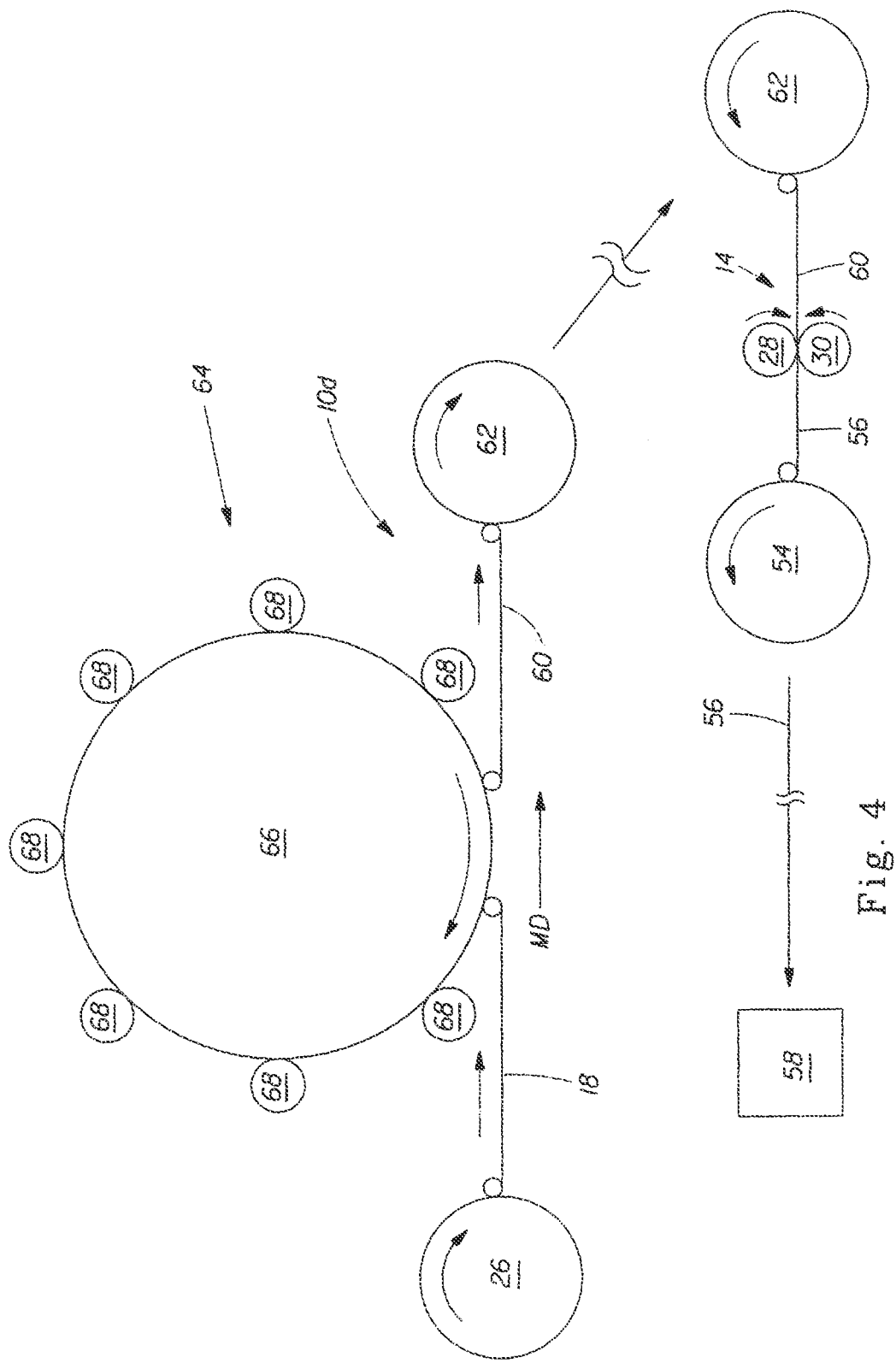
FIG. 4 is a sectional view of yet another alternative embodiment of an exemplary web substrate printing and apparatus for imparting elastic-like behavior.

Alternatively, as shown in FIG. 4, the printed web substrate 60 can alternatively be wound into intermediate parent roll 62. Upon a defined need of a printed and elastic-like, structurally modified web substrate 56, the printed web substrate 60 disposed about intermediate parent roll 62 can be then processed separately by apparatus for printing and imparting elastic-like behavior 10. The resulting printed and textured web substrate 56 can be then wound about an additional second parent roll 54 for storage or, alternatively, directed immediately to any manufacturing process 58 as required. In any regard, it should be realized by those of skill in the art that the step of applying indicia 72 applied to a web substrate 18 by flexographic printing apparatus 64 and the step of providing elastic-like behavior to the web substrate 18 by apparatus for printing and imparting elastic-like behavior 10 can be presented as concurrent steps in a singular process or as individualized steps as needed by the end user.

Additionally, it should be realized that web substrate 18 of the present invention may comprise polyolefins, such as polyethylenes including linear low density polyethylene (LLDPE), low density polyethylene (LDPE), ultra low density polyethylene (ULDPE), high density polyethylene (HDPE), or polypropylene and blends thereof with the above and other materials. Examples of other suitable polymeric materials suitable for use in the instant invention and for providing a containment for a plurality of desired consumer product include other suitable polymeric materials, such as polyester, polyurethanes, compostable or biodegradable polymers, heat shrink polymers, thermoplastic elastomers, metallocene catalyst based polymers, and breathable polymers. Further, the web substrate 18 of the present invention may also comprise a synthetic woven, synthetic knit, non-woven, aperture film, microscopically expanded three-dimensional formed films, absorbent or fibrous absorbent materials, foam filled compositions, laminates, and/or combinations thereof. Any non-wovens may be spun laced, spun bond, melt blown, carded, and/or air-through or calender bonded. Additionally, material suitable for web substrate 18 of the present invention may be cellulose based.

As shown in FIG. 7, suitable consumer products 74 of the instant invention may include towels, towel substrates, tissues, tissue substrates, wipes, disposable diapers, sanitary napkins, as well as other absorbent articles. Additionally, printed and textured web substrate 56 may be disposed about a plurality of consumer products 74 in a manufacturing process 58 that includes flow wrapping, over wrapping, and any other process known to those of skill in the art suitable for use in binding a plurality of consumer articles into a marketable consumer unit. Such marketable consumer units may contain a plurality of individually wrapped paper toweling, bath tissues, facial tissues, diapers, sanitary napkins, tampons, and the like.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for deforming a web substrate and depositing a material on said web substrate, the process comprising the steps of:
   providing a web substrate consisting essentially of polymeric material;
   providing a source of the material to be deposited onto the web substrate;
   feeding said web substrate between a pair of intermeshing rolls wherein at least one of said rolls has a plurality of teeth thereon to provide said web substrate with a plurality of undeformed first regions and a plurality of second regions comprising the same material composition, wherein said second regions are formed by said teeth and comprise a plurality of deformations; and
   depositing said material onto said web substrate while said material is in contact with at least one of said intermeshing rolls so that said material is in registration with one of the following portions of the web substrate: at least some of said undeformed first regions, or at least some of said deformations comprising said second regions.

2. The process of claim 1 wherein the material is deposited only on said deformations.

3. The process of claim 1 wherein the material is deposited only on undeformed first regions between said deformations.

4. The process of claim 1 wherein said deformations comprise a plurality of raised rib-like elements.

5. The process of claim 4 wherein said first regions and second regions provide the web substrate with elastic-like behavior wherein said first regions undergo a molecular level and geometric deformation and said second regions initially undergo a substantially geometric deformation when said web material is subjected to an applied elongation along at least one axis.

6. The process of claim 1 wherein said web substrate comprises a nonwoven, and said deformations comprise a plurality of tufts.

7. The process of claim 1 wherein the material comprises an ink.

8. The process of claim 1 wherein the material comprises a lotion.

9. The process of claim 1 wherein the material comprises a glue.

10. The process of claim 7 wherein the step of depositing a material on said web substrate comprises printing ink on said web substrate.

11. The process of claim 1 wherein the material is deposited on said web substrate simultaneously with providing said web substrate with a plurality of first regions and a plurality of second regions.

12. A process for deforming a web substrate and depositing a material on said web substrate, the process comprising the steps of:
    providing a web substrate;
    providing a source of the material to be deposited onto the web substrate;
    feeding said web substrate between a pair of intermeshing rolls wherein at least one of said rolls has a plurality of teeth thereon, and at least one of the intermeshing rolls has a plurality of conduits therein that are in fluid communication with the source of the material to be deposited onto the web substrate; and
    providing said web substrate with a plurality of undeformed first regions and a plurality of second regions comprising the same material composition when said web substrate is fed between said intermeshing rolls, wherein said second regions are formed by said teeth and comprise a plurality of deformations, and depositing the material on said web substrate through said conduits so that said material is in registration with one of the following portions of the web substrate: at least some of said undeformed first regions, or at least some of said deformations comprising said second regions.

* * * * *